United States Patent [19]

Laver

[11] Patent Number: Plant 6,054

[45] Date of Patent: Dec. 8, 1987

[54] ROSE PLANT NAMED LAVCALE

[75] Inventor: Keith Laver, Caledon East, Canada

[73] Assignee: Nor'East Miniature Roses, Inc., Rowley, Mass.

[21] Appl. No.: 801,700

[22] Filed: Nov. 25, 1985

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of unusually stable red flower covering.

1 Drawing Figure

The present invention relates to a new and distinct variety of rose plant of the miniature rose class, which is a cross of the rose known as "Party Girl" as seed parent and the rose known as "Dwarfking 78" as pollen parent. The varietal denomination of this new variety is "Lavcale".

Among the novel characteristics possessed by this new variety which distinguish it from the cultivar from which it sported and all other varieties of which I am aware are its flowers of unusually stable red flower coloring that holds well from bud stage through opening stages and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "45A" is plate 45A of The Royal Horticultural Society Colour Chart.

Parentage:

*Seed parent.*—"Party Girl".

*Pollen parent.*—"Dwarfking 78".

Class: Miniature.

The following observations are made of specimens grown outdoors in Essex County, Mass., during the month of August.

FLOWER

Blooming habit: Recurrent.

A. Bud:

(1) *Size.*—Medium.

(2) *Form.*—Globular.

(3) *Color.*—When sepals first divide — bud color appears near 45A to currant red 46A. Color is very stable and is maintained as petals unfurl.

(4) *Sepals.*—Longer than bud, foliated.

(5) *Peduncle.*—Length — about $\frac{7}{8}$ inch. Aspect — straight. Strength — erect. Color — near 144A.

B. Bloom:

(1) *Size.*—Average size when fully expanded — about $1\frac{1}{4}$ to $1\frac{1}{2}$ inches.

(2) *Borne.*—Primarily singly.

(3) *Form.*—Cupped, becoming flat.

(4) *Petalage.*—Number of petals under normal conditions — about 30 to 35.

(5) *Color.*—After sepals fall, flowers open retaining bud coloring, near 45A to 46A. Red flower coloring is unusually stable through stages of development and aging.

C. Petals:

(1) *Texture.*—Average.

(2) *Appearance.*—Inside — satiny, outside — matte.

(3) *Form.*—Wide, fan shaped.

(4) *Arrangement.*—Regularly arranged, imbricated.

(5) *Petaloids in center.*—Medium.

(6) *Persistence.*—Drop off cleanly.

(7) *Fragrance.*—None.

(8) *Lasting quality.*—Very long on plant and as cut flower.

REPRODUCTIVE ORGANS

A. Stamens, filaments and anthers:

(1) *Arrangement.*—Regularly arranged around styles.

(2) *Color.*—Near 17B.

B. Pollen:

*Color.*—Near 17A.

C. Styles: Even length, thin.

D. Stigmas:

*Color.*—Near 185C.

E. Hips: None observed.

PLANT

A. Form: Upright, compact.

B. Growth: Very vigorous, uniform branching.

*Height attained.*—About 12 to 15 inches.

C. Foliage: Compound 5 to 7 leaflets.

(1) *Size.*—Medium.

(2) *Quantity.*—Abundant.

(3) *Color.*—New foliage: Upper side — near to 137B. Under side — near to 138B. Old foliage: Upper side — near 139A. Under side — near 138B.

(4) *Shape.*—Oval, pointed.

(5) *Texture.*—Upper side is glossy and under side is matte.

(6) *Edge.*—Serrated.

(7) *Serration.*—Serrate.

(8) *Leaf stem.*—Color — near 141B. Under side — near 144C.

(9) *Stipules.*—Medium, slightly bearded.

(10) *Resistance to disease.*—Blackspot — average. Mildew — average. Rust — average.

D. Wood:

(1) *New wood.*—Color — near 148A. Bark — smooth.

(2) *Old wood.*—Color — near 137A. Bark — smooth.

E. Thorns:

(1) *Thorns.*—Quantity (main stalk) — ordinary. On laterals from stalk — ordinary. Form — long, thin, straight, pointed. Length — medium. Color — near 184A. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized by unusually stable red flower coloring, near currant red, which maintains color through flower development and aging.

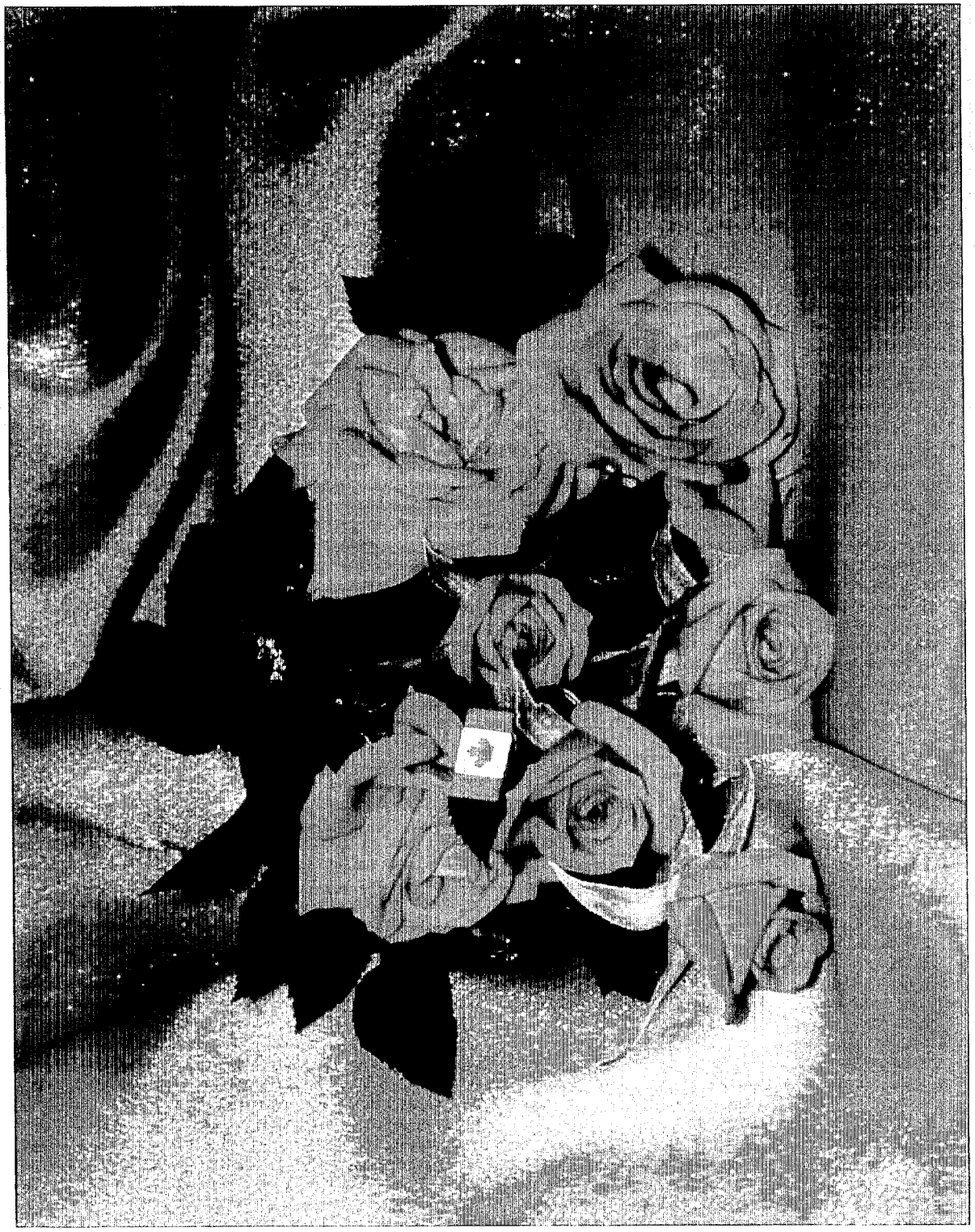

* * * * *